(12) United States Patent
Li et al.

(10) Patent No.: US 10,507,250 B2
(45) Date of Patent: Dec. 17, 2019

(54) PRECURSOR OF A HISTONE DEACETYLASE INHIBITOR PET IMAGING COMPOUND FOR TRACKING CEREBRAL NEURODEGENERATIVE AND TUMOR DISEASES

(71) Applicant: INER, Atomic Energy Council, Executive Yuan, Taoyuan OT (TW)

(72) Inventors: Ming-Hsin Li, Taoyuan (TW);
Chyng-Yann Shiue, Taoyuan (TW);
Han-Chih Chang, Taoyuan (TW);
Chun-Fang Feng, Taoyuan (TW)

(73) Assignee: Institute of Nuclear Energy Research, Atomic Energy Council, Executive Yuan, Taoyuan (TW)

( * ) Notice: Subject to any disclaimer, the term of this patent is extended or adjusted under 35 U.S.C. 154(b) by 9 days.

(21) Appl. No.: 15/698,672

(22) Filed: Sep. 8, 2017

(65) Prior Publication Data
US 2019/0076552 A1 Mar. 14, 2019

(51) Int. Cl.
*A61K 49/04* (2006.01)
*A61K 49/00* (2006.01)
*G06T 7/00* (2017.01)
*G01T 1/29* (2006.01)
*A61K 51/00* (2006.01)
*G06T 7/40* (2017.01)

(52) U.S. Cl.
CPC .......... *A61K 49/0004* (2013.01); *A61K 51/00* (2013.01); *G01T 1/2985* (2013.01); *G06T 7/0012* (2013.01); *G06T 7/40* (2013.01); *G06T 2207/10104* (2013.01); *G06T 2207/30016* (2013.01)

(58) Field of Classification Search
None
See application file for complete search history.

(56) References Cited

U.S. PATENT DOCUMENTS

2009/0124631 A1* 5/2009 Li ................. A61K 31/337
514/253.01

* cited by examiner

*Primary Examiner* — James W Rogers

(57) ABSTRACT

Method provided for labeling a nuclear medicine for imaging tracing, comprising a labeling precursor of the HDAC inhibitor BNL-26 (C22H23N3O) and the derivatives that are separated into two classes. The first class comprises a BNL-26 (C22H23N3O) and derivatives BNL-26a (C21H21N3O), BNL-26b (C22H22N2O), and other compounds of the labeling precursors which are categorized into two parts, the first part includes BNL-26-CH2CH2OTs (C31H33N3O4S), BNL-26a-CH2CH2OTs (C30H31N3O4S), and BNL-26b-CH2CH2OTs (C31H32N2O4S), which provides labeling precursor through —CH2CH2OTs structure, and the second part includes pre-BNL-26 (C28H34N3O3B), pre-BNL-26a (C27H32N3O3B), pre-BNL-26b (C28H33N2O3B), which provides labeling precursor through 4,4,5,5-tetramethyl-1,3, 2-dioxaborolan-2-yl structure. The second class includes BNL-26 (C22H23N3O) indole/indoline, which provides a series of derivative labeling precursors derived from a secondary amide bond.

1 Claim, No Drawings

PRECURSOR OF A HISTONE DEACETYLASE INHIBITOR PET IMAGING COMPOUND FOR TRACKING CEREBRAL NEURODEGENERATIVE AND TUMOR DISEASES

BACKGROUND OF THE INVENTION

Field of the Invention

The present invention relates to a method for labeling a nuclear precursor for imaging tracing, particularly to a method for production of a precursor of the HDAC inhibitor BNL-26 (C22H23N3O) and the derivatives.

Description of Related Art

Neurodegenerative diseases are a disease state in which neurons in the brain and spinal cord are lost, and since neuronal cells do not have regenerative capacity, excessive damage can lead to dysfunction disease, such as Alzheimer, Parkinson's and Huntington's diseases.

The histone deacetylase inhibitor (HDACi) is a drug for inhibition of histone deacetylase function of human body. The medical research has been studying the treatment of neurodegenerative diseases through the histone deacetylase Inhibitors. In recent years, the study also indicated that the effect of chromatin modification in brain cells has a role in memory formation, and HDAC enzymes plays a key role that mice with abnormal enzyme secretion will suffer from memory loss, and the human suffering of cranial nerve degeneration disease also has a similar situation in the brain.

In recent years, the medical industry has also studied the use of histone deacetylase inhibitor for cancer treatment. The specific mechanisms of these inhibitors the literature suggests possible epigenetics route, such as Richon et al. found that HDAC inhibitors can mediate p21 (WAF1) to regulate p53 tumor suppression function. The current cancer treatments include drug treatment, surgical resection and radiation therapy are the three major options. On the drug treatment, although the general effect of chemotherapy drugs may kill cancer cells, but the normal cells are also poisoned during the treatment process, therefore, the major international pharmaceutical companies focus on fully developed target therapy treatment to accurately diminish cancer cells. In recent years, the medical industry has also studied the use of histone deacetylase inhibitor for cancer treatment. The specific mechanisms of these inhibitors the literature suggests possible epigenetics route, such as Richon et al. found that HDAC inhibitors can mediate p21 (WAF1) to regulate p53 tumor suppression function.

The current cancer treatments include drug treatment, surgical resection and radiation therapy are the three major options. On the drug treatment, although the general effect of chemotherapy drugs may kill cancer cells, but the normal cells are also poisoned during the treatment process, therefore, the major international pharmaceutical companies focus on fully developed target therapy treatment to accurately diminish cancer cells. Target therapy treatment has shown a rapid growth since 2004 for its significant medical results. Sales volume of target therapy is only $ 5 billion in the market 2005, it is expected to reach around 60 billion USD by 2025. Therefore, the histone deacetylase inhibitors (HDAC inhibitors) will be a new hope for the future in treatment of malignant neoplasms and neurodegenerative diseases.

Conventional studies about cancer and development dysplasia of organs like colon, rectum, cervix, stomach, and prostate have not been a satisfactory outcome. Besides, the research of natural aging indicates that cerebral atrophy is an early sign of neurodegeneration related to cognitive deficit and loss of memory, and dementia like Alzheimer's disease usually leads the patient of such disease to an unrecoverable situation for unknown causes and lacking of a measure of early diagnosis of Alzheimer's disease. And early discovery, diagnosis, and curing of cancer and Alzheimer's disease depend on diagnostic methods is still in vain. In the prior art, U.S. Pat. No. 7,868,205 disclosed that o-amino benzamide HDAC inhibitors had a much bigger but flat aromatic and heteroaromatic substituents such as phenyl, furyl, thienyl and the like para to the amino moiety.

According to research in cancer and development dysplasia of body organs, over-expression of histone deacetylase 2 (HDAC-2) does exist in both cases and in many cases of those diseases, such as colon, rectum, cervix, stomach, and prostate etc. Furthermore, the research in recent years also pointed out that chromatin modification in the brain cells is related to the memory formation which is influenced intensely by histone deacetylase, for example, a mouse with abnormal secretion of histone deacetylase enzyme could lose part of memory as same as the symptom of Alzheimer's disease. Thus, dosing histone deacetylase inhibitors will be a new hope to the treatment of cancer and Alzheimer's disease.

HDAC inhibitors have been a hot spot of medication research as a targeted anti-tumor medication. The existing HDAC inhibitors are mainly divided into four categories according to structure, comprising: (a) hydroxamic acids, suchlike Vorinostat; (b) cyclic tetrapeptide, suchlike Romidepsin (FK228) and depsipeptide; (c) benzoylamide, suchlike MS-275 and SC-027; (d) short-chain fatty acid, suchlike valproic acid and butyrate. The efficacies of HDAC inhibitors for treating hematologic malignancies and solid tumors are confirmed both in vivo and vitro experiments. The vitro experiment confirmed that HDAC inhibitors exhibits good anti-tumor effect to the tumor cell of bladder, bone, breast, uterus, central nervous system, esophagus, lung, ovary, pancreas, or prostate by tumor cell apoptosis, proliferation inhibition and cell cycle arrest, and many types of HDAC inhibitors are entering phase I or II or III of clinical study for their multiple paths and high efficiencies for anticancer.

Vorinostat (suberoylanilide hydroxamic acid, SAHA) and Romidepsin (cyclic peptide) are approved by FDA to be listed for applying to cutaneous T-cell lymphoma (CTCL) and the application of the treatment of solid tumor is also in clinical trials. The benzoylamide HDAC inhibitors chidamide developed by Chipscreen Ltd. is approved by FDA for clinical research in USA to confirm that the new type HDAC inhibitors in small doses and low concentration can induce tumor cell differentiation and selective apoptosis for antitumor proliferation and be non-toxic to normal cells.

By analysis of tumor diagnoses in identification of whether a tumor exists, the nature of tumors, benign or malignant ones, phase of tumor stage and metastasis are all very important, it revealed that most tumors are often found lately, and at the time it has already caused damage to one or more functions of vital organs, and even has been transferred to the entire body. Therefore, the key question is how to treat tumor in early detections, but detection of tumors in earlier stage is still very difficult.

Diagnosis of Alzheimer's disease (referred to as AD) includes basic check neuropsychological tests, blood routine, biochemical test of liver and kidney functions, vitamin B12 level, thyroid function, syphilis serology, and brain computed tomography or magnetic resonance angiography. High order PET positron imaging diagnostic methods exploiting amyloid hypothesis as the theoretical basis for drugs include F-18-AV45 and F-18-PIB two kinds, whereas the microtubule associated protein hypothesis (Tau hypothesis) as the theoretical basis for drug is not yet available.

Clinical diagnosis with imaging inspection includes X-ray examination, ultrasonography, magnetic resonance imaging, X-ray tomography (abbreviated CT) and radioisotope examination. Early diagnosis of tumor and Alzheimer's disease has a role of important significance, because only a early diagnosis and treatment can get better result of treatment. However, due to various objective and subjective reasons, the majority of patients in the treatment or diagnosis of tumors that already advanced in midterm or later, and the treatment effect is not satisfactory in this case. Although the diagnosis method of tumor is developing rapidly, but many tumor screening methods are not effective enough, and it takes that tumors need to be of 1~1.5 cm in diameter size before it can be clearly displayed in an imaging inspection.

A general blood test accuracy is insufficient, for example, a prostate-specific antigen (PSA) is a glycoprotein. This antigen can only be produced by prostate cells, when a prostate disease occurs, such as prostate tumor, a prostate hyperplasia cell will produce an excess of PSA that leads to the PSA level in the blood increases. Doctors may analyze blood PSA levels to determine the possibility of patients suffering from a prostate tumor. There are various factors leading to elevated PSA, such as prostate infection and benign prostate hyperplasia. Moreover, not all prostate cancer patients exhibited elevated PSA, thus a PSA test result can not be confirmed for a candidate of prostate cancer patient. Diagnosis of Alzheimer's disease with the latest PET drugs F-18-AV45 and F-18-PIB, the imaging of PET can only be diagnosed whether an Alzheimer's disease exists, however, human aging phenomenon also reveals an identical reaction with the same image, and thus it is difficult to confirm that a patient is suffering from Alzheimer's disease with the image presented.

SUMMARY OF THE INVENTION

The primary object of the present invention is to provide precursors of nuclear medical imaging compound, in which additional four compounds, such as HDAC inhibitor BNL-26 (C22H23N3O) and derivatives BNL-26a (C21H21N3O), BNL-26b (C22H22N2O) and the like, are labeled with radioactive nuclei F-18. A series of novel nuclear medical imaging compounds, such as BNL-26-CH2CH218F, BNL-26a-CH2CH218F and BNL-26b-CH2CH218F and the like, which are used in combination with the overexpression of the histone deacetylase in human body for nuclear medical imaging tracing and treatment of tumor.

Another object of the present invention aims to provide a method for labeling a nuclear medicine for image tracing, comprising a nuclear labeling precursor of the HDAC inhibitor BNL-26 (C22H23N3O) and the derivatives that are separated into two classes. The first class comprises a BNL-26 (C22H23N3O) and derivatives BNL-26a (C21H21N3O), BNL-26b (C22H22N2O), and other compounds of the labeling precursors which are categorized into two parts, the first part includes, such as, BNL-26-CH2CH2OTs (C31H33N3O4S), BNL-26a-CH2CH2OTs (C30H31N3O4S), and BNL-26b-CH2CH2OTs (C31H32N2O4S), which provides labeling precursor through —CH2CH2OTs structure, and the second part includes, such as, pre-BNL-26 (C28H34N3O3B), pre-BNL-26a (C27H32N3O3B), pre-BNL-26b (C28H33N2O3B), which provides labeling precursor through 4,4,5,5-tetramethyl-1,3,2-dioxaborolan-2-yl structure. The second class includes BNL-26 (C22H23N3O) indole/indoline, which provides a series of derivative labeling precursors derived from a secondary amide bond.

Another object of the present invention aims to provide a novel compound for the diagnosis of malignant neoplasms and neurodegenerative diseases through utilizing the characteristic of the positron decay of the fluoro-18 or zirconium-89 isotopes, in which when the decaying release of the positron encounters the electrons of the cell produces an "annihilation reaction", and a pair of opposite directions of 511 keV Gamma rays were formed and images were obtained by positron emission tomography (PET) for treatment of malignant tumor and neurodegenerative diseases.

Another object of the present invention aims to provide a method of diagnosis of tumors through combination of HDAC targets with a chemotherapeutic agent, such as Indoline, to reduce the dose and enhance the therapeutic effect.

DETAILED DESCRIPTION OF THE PREFERRED EMBODIMENTS

Method provided for labeling a nuclear medicine for imaging tracing, comprising a labeling precursor of the HDAC inhibitor BNL-26 (C22H23N3O) and the derivatives, which are separated into two classes. The first class comprises a BNL-26 (C22H23N3O) derivative BNL-26a (C21H21N3O), BNL-26b (C22H22N2O) and other compounds of the labeling precursors which are categorized into two parts, the first part includes BNL-26-CH2CH2OTs (C31H33N3O4S), BNL-26a-CH2CH2OTs (C30H31N3O4S), and BNL-26b-CH2CH2OTs (C31H32N2O4S) and the like, which provides labeling precursor through —CH2CH2OTs structure, and the second part includes pre-BNL-26 (C28H34N3O3B), pre-BNL-26a (C27H32N3O3B), pre-BNL-26b (C28H33N2O3B), which provides labeling precursor through 4,4,5,5-tetramethyl-1,3,2-dioxaborolan-2-yl structure. The second class includes BNL-26 (C22H23N3O) indole/indoline, which provides a series of derivative labeling precursors derived from a secondary amide bond. These two types of precursors were used for the radioactive nuclei F-18 labeling on the backend to form a series of novel nuclear medical tracers to be formed.

The group 1 of the precursors having HDAC inhibitor BNL-26 and the derivatives of the present invention includes the structures as shown in Table 1 below.

TABLE 1

| Code | IUPAC | Structure |
|---|---|---|
| BNL-26-CH2CH2OTs | 2-((3-(4-((dimethylamino)methyl)benzamido)-[1,1'-biphenyl]-4-yl)amino)ethyl 4-methylbenzenesulfonate | 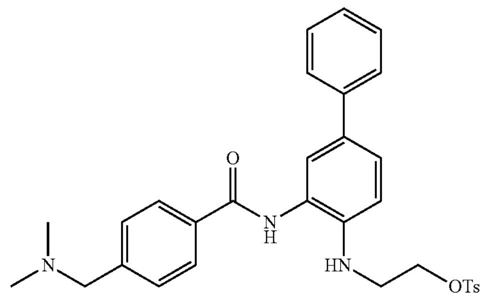 [SMILES: Cc1ccc(S(=O)(=O)OCCNc2ccc(-c3ccccc3)cc2NC(=O)c2ccc(CN(C)C)cc2)cc1] |
| BNL-26a-CH2CH2OTs | 2-((3-(4-(dimethylamino)benzamido)-[1,1'-biphenyl]-4-yl)amino)ethyl 4-methylbenzenesulfonate | 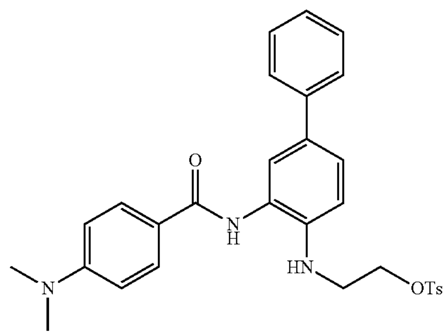 [SMILES: Cc1ccc(S(=O)(=O)OCCNc2ccc(-c3ccccc3)cc2NC(=O)c2ccc(N(C)C)cc2)cc1] |
| BNL-26b-CH2CH2OTs | 2-((3-(4-isopropylbenzamido)-[1,1'-biphenyl]-4-yl)amino)ethyl 4-methylbenzenesulfonate | 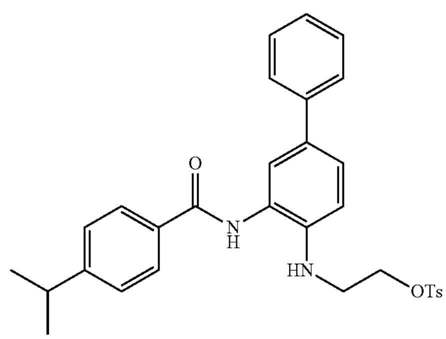 [SMILES: Cc1ccc(S(=O)(=O)OCCNc2ccc(-c3ccccc3)cc2NC(=O)c2ccc(C(C)C)cc2)cc1] |
| BNL-26c-CH2CH2OTs | 2-((3-(4-isobutylbenzamido)-[1,1'-biphenyl]-4-yl)amino)ethyl 4-methylbenzenesulfonate | 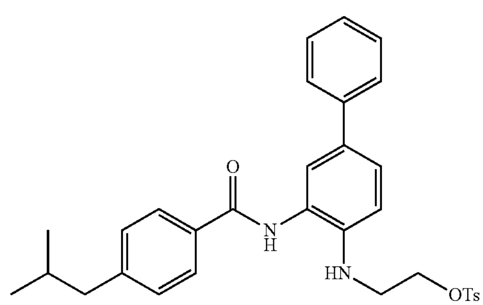 [SMILES: Cc1ccc(S(=O)(=O)OCCNc2ccc(-c3ccccc3)cc2NC(=O)c2ccc(CC(C)C)cc2)cc1] |
| BNL-26d-CH2CH2OTs | 2-((3-(4-propylbenzamido)-[1,1'-biphenyl]-4-yl)amino)ethyl 4-methylbenzenesulfonate | 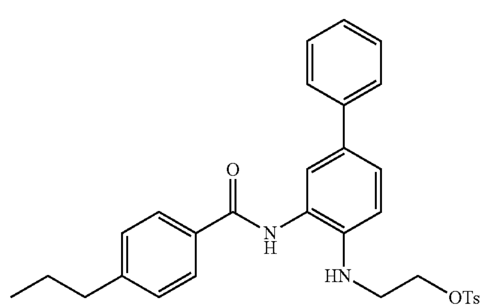 [SMILES: CCCc1ccc(C(=O)Nc2cc(-c3ccccc3)ccc2NCCOS(=O)(=O)c2ccc(C)cc2)cc1] |

TABLE 1-continued
| Code | IUPAC | Structure |
|---|---|---|
| pre-BNL-26 | N-(4-amino-4'-(4,4,5,5-tetramethyl-1,3,2-dioxaborolan-2-yl)-[1,1'-biphenyl]-3-yl)-4-((dimethylamino)methyl)benzamide | 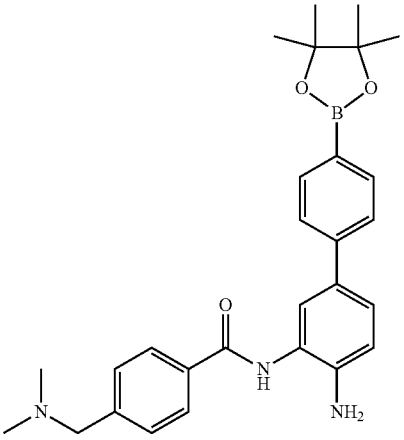 |
| pre-BNL-26a | N-(4-amino-4'-(4,4,5,5-tetramethyl-1,3,2-dioxaborolan-2-yl)-[1,1'-biphenyl]-3-yl)-4-(dimethylamino)benzamide | 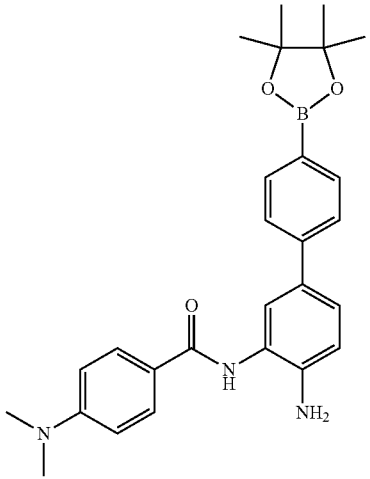 |
| pre-BNL-26b | N-(4-amino-4'-(4,4,5,5-tetramethyl-1,3,2-dioxaborolan-2-yl)-[1,1'-biphenyl]-3-yl)-4-isopropylbenzamide | 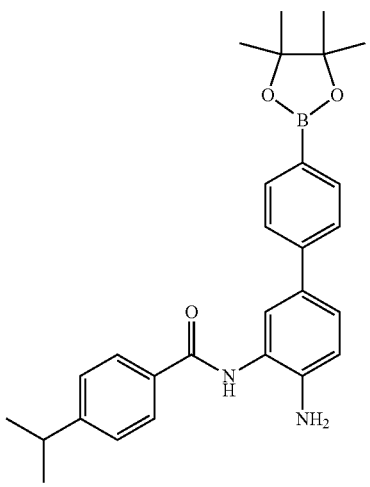 |

TABLE 1-continued

| Code | IUPAC | Structure |
|---|---|---|
| pre-BNL-26c | N-(4-amino-4'-(4,4,5,5-tetramethyl-1,3,2-dioxaborolan-2-yl)-[1,1'-biphenyl]-3-yl)-4-isobutylbenzamide | 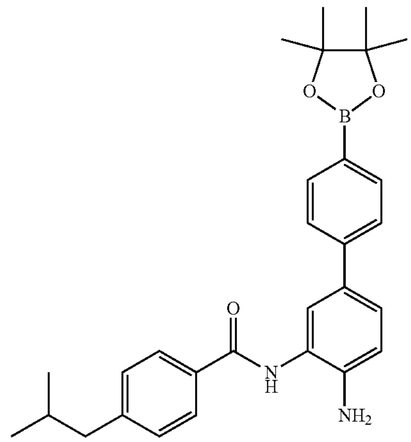 |
| pre-BNL-26d | N-(4-amino-4'-(4,4,5,5-tetramethyl-1,3,2-dioxaborolan-2-yl)-[1,1'-biphenyl]-3-yl)-4-propylbenzamide | 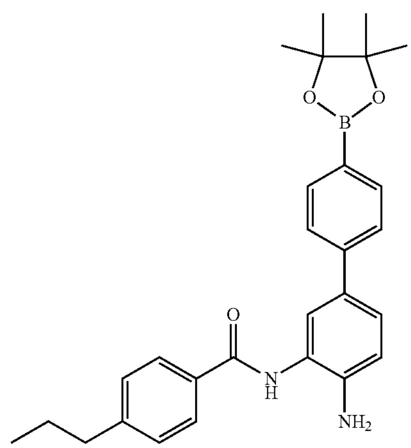 |

The synthesis of the precursors shown above is carried out by the steps described below.

(4-hydroxyphenyl) boronic acid was reacted with 5-chloro-2-nitroaniline by heating Pd (OAc) 2, K3PO4 in DMF: H2O=1:1 for 3 hours to form 3'-amino-4'-nitro-[1,1'-biphenyl]-4-ol,

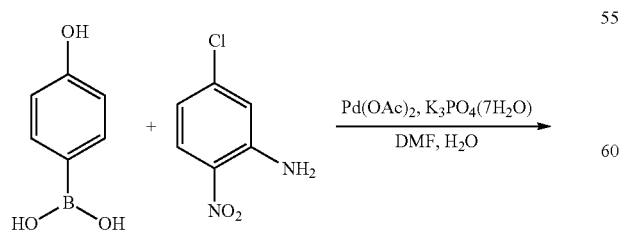

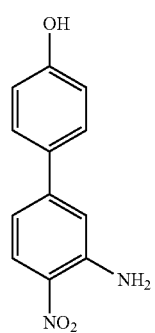

The —OH group in the 3'-amino-4'-nitro-[1,1'-biphenyl]-4-ol structure was protected with -MOM and subjected to low temperature reaction with DIPEA in DCM solution at a temperature of 0-20° C. to form 4'-(methoxymethoxy)-4-nitro-[1,1'-biphenyl]-3-amine,

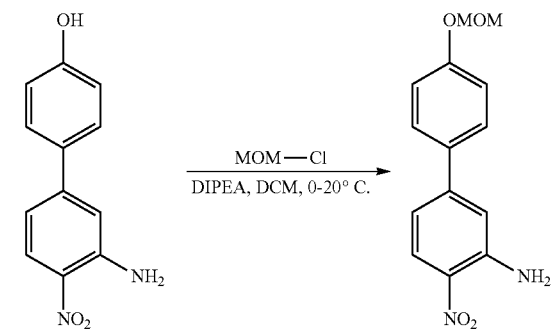

4'-(methoxymethoxy)-4-nitro-[1,1'-biphenyl]-3-amine with R group-containing p-phenylcarboxylic acid is provided to carry out the nucleophilic substitution reaction in DCM and DMF solution with coupling regent HOBt, DMAP, EDCl, forming (4'-(methoxymethoxy)-4-nitro-[1,1'-biphenyl]-3-yl) benzamide with a R group, wherein the R group is a substituent such as —CH2N (CH3) 2, —N(CH3) 2, —CH2CH (CH3) 2, —CH (CH3) 2, —CH2CH2CH3,

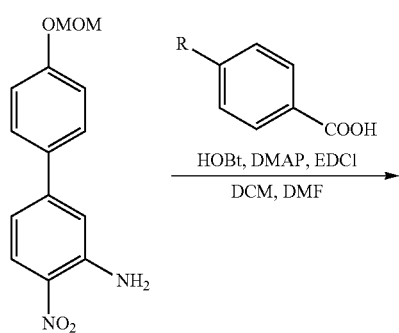

(4'-(methoxymethoxy)-4-nitro-[1,1'-biphenyl]-3-yl) benzamide with R group is heated with iron powder, acetic acid in ethanol with water, and nitro is reduced to an amine group to form N-(4-amino-4'-(methoxymethoxy)-[1,1'-biphenyl]-3-yl) benzamide with R group,

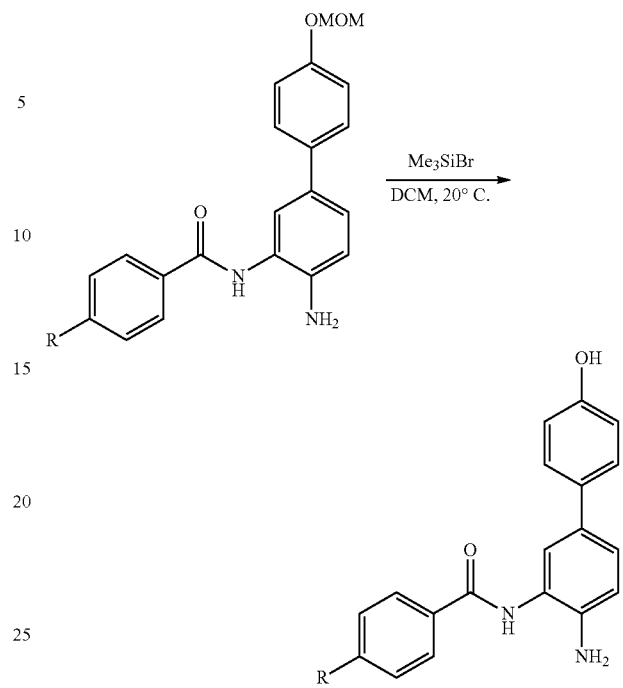

(4-amino-4'-(methoxymethoxy)-[1,1'-biphenyl]-3-yl) benzamide with R group was treated with Me3SiBr in DCM solution to remove -MOM protection, forming (4-amino-4'-hydroxy-[1,1'-biphenyl]-3-yl) benzamide with a R group at a temperature of 20° C.,

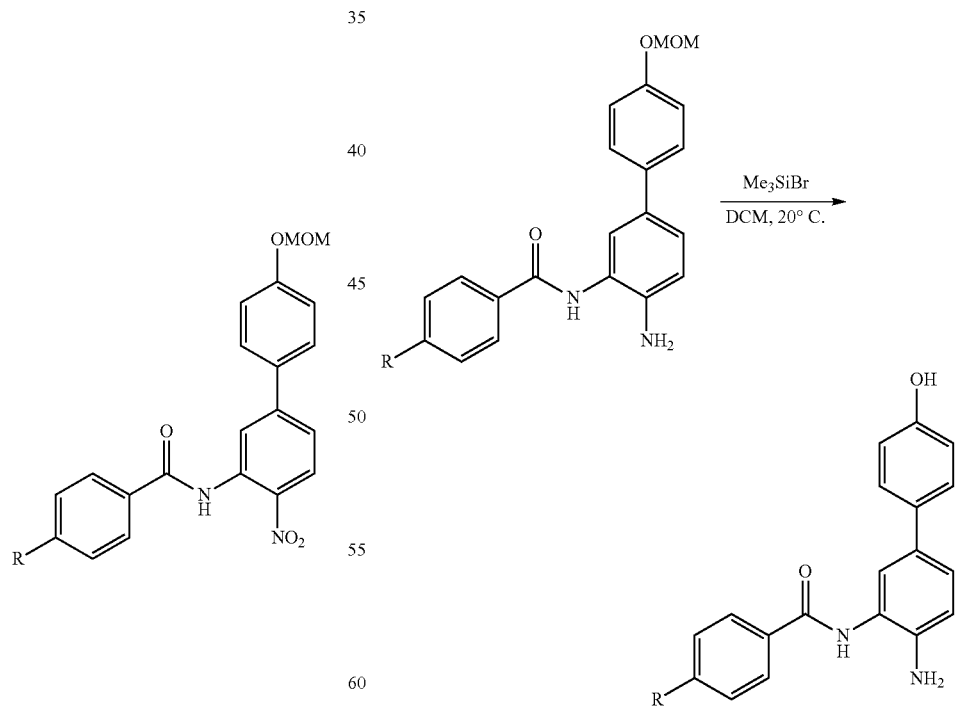

(4-amino-4'-hydroxy-[1,1'-biphenyl]-3-yl) benzamide with R group in the presence of Tf2O in a pyridine solution at low temperature to convert the —OH group to —OTf Group to form 4'-amino-3'-benzamido-[1,1'-biphenyl]-4-yl trifluoromethanesulfonate with R group:

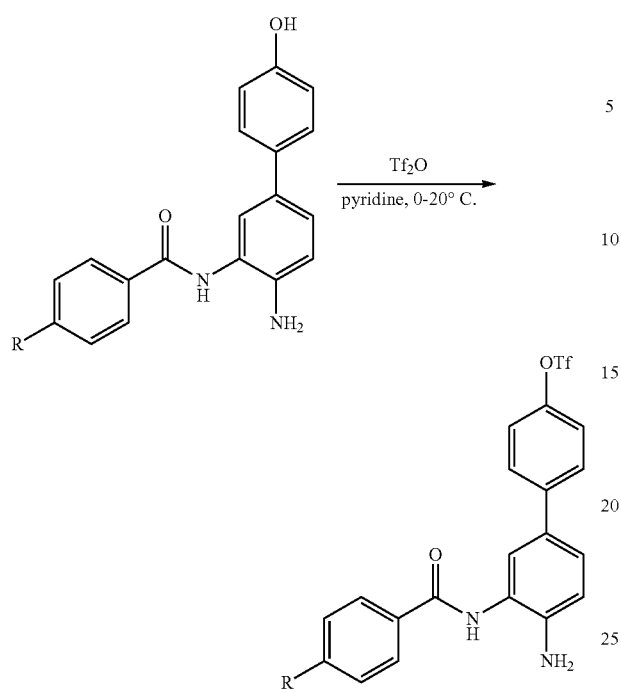

A-4'-amino-3'-benzamido-[1,1'-biphenyl]-4-yl trifluoromethanesulfonate with R group was treated with 4P—Pd-1 (dba)3, Xphos, KOAc in dioxane solution, and the —OTf was substituted with 4,5,5-tetramethyl-1,3,2-dioxaborolane at a temperature about 90° C. to form a precursor with R group: (N-(4-amino-4'-(4,4,5,5-tetramethyl-1,3,2-dioxaborolan-2-yl)-[1,1'-biphenyl]-4-yl) benzamide:

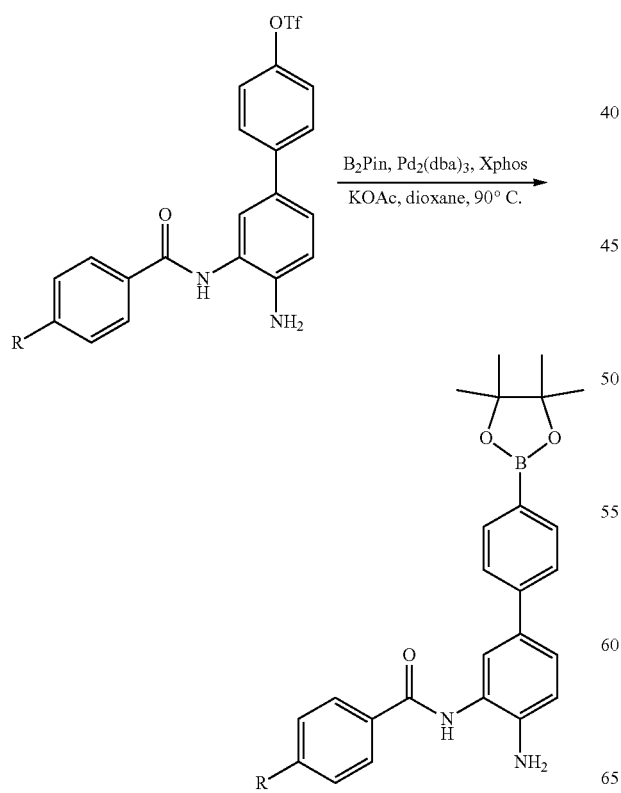

The group 2 of the precursors having HDAC inhibitor BNL-26 and the derivatives of the present invention consisting of replacing the Benzene of the precursors of F-18-BNL-26 and the derivatives with Pyridine:

1. Replace A ring of Benzene with Pyridine, as follows:

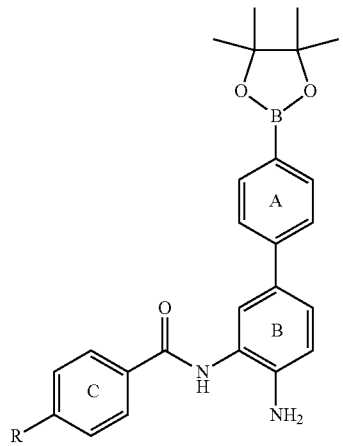

TABLE 2-1

| Code | Structure |
|---|---|
| pre-Iner-1 | (structure shown) |
| pre-Iner-2 | (structure shown) |

TABLE 2-1-continued
| Code | Structure |
|------|-----------|
| pre-Iner-3 | 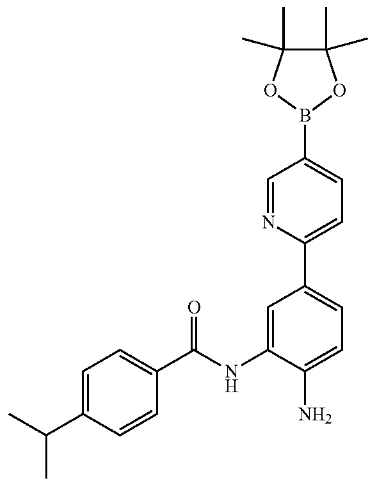 |
| pre-Iner-4 | 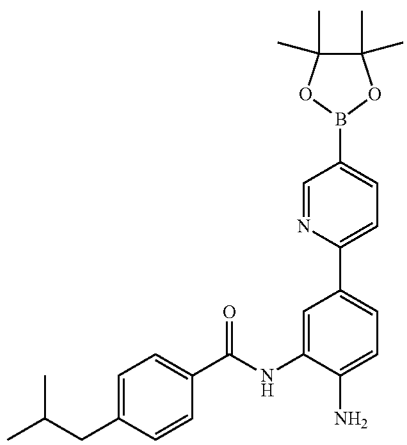 |
| pre-Iner-5 | 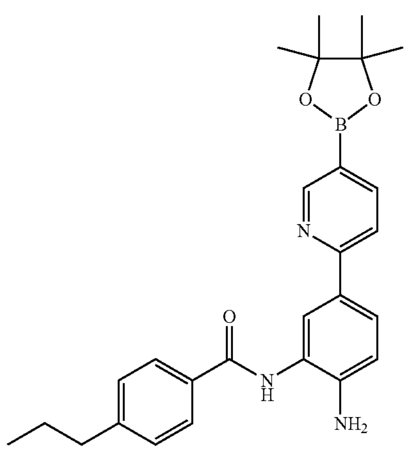 |
| pre-Iner-6 | 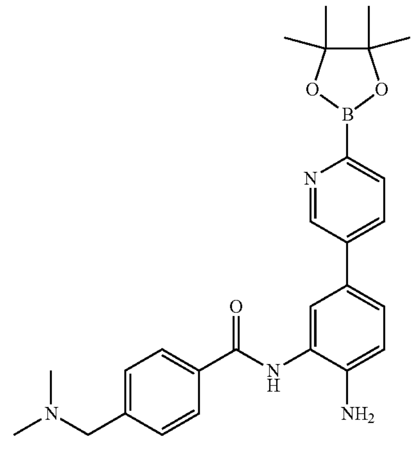 |
| pre-Iner-7 | 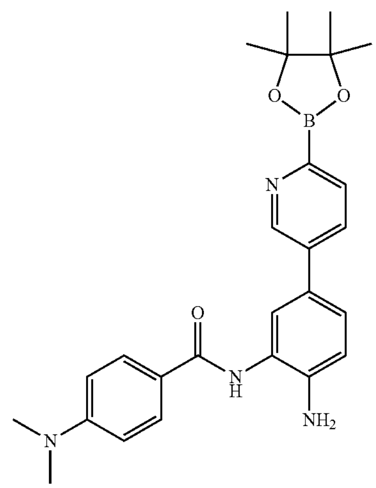 |
| pre-Iner-8 | 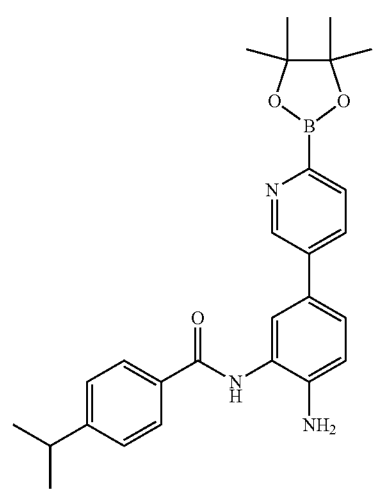 |
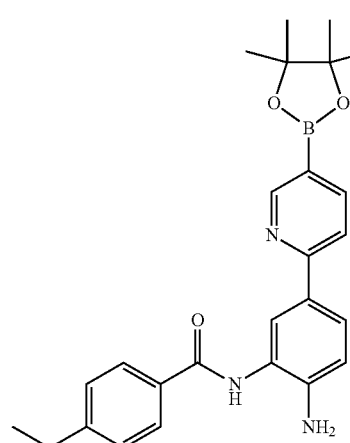

TABLE 2-1-continued
| Code | Structure |
|---|---|
| pre-Iner-9 | 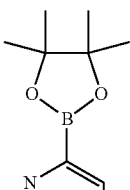 |
| pre-Iner-10 | 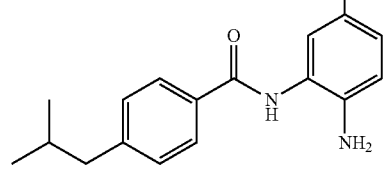 |
2. Replacing B ring of Benzene with Pyridine, as follows:
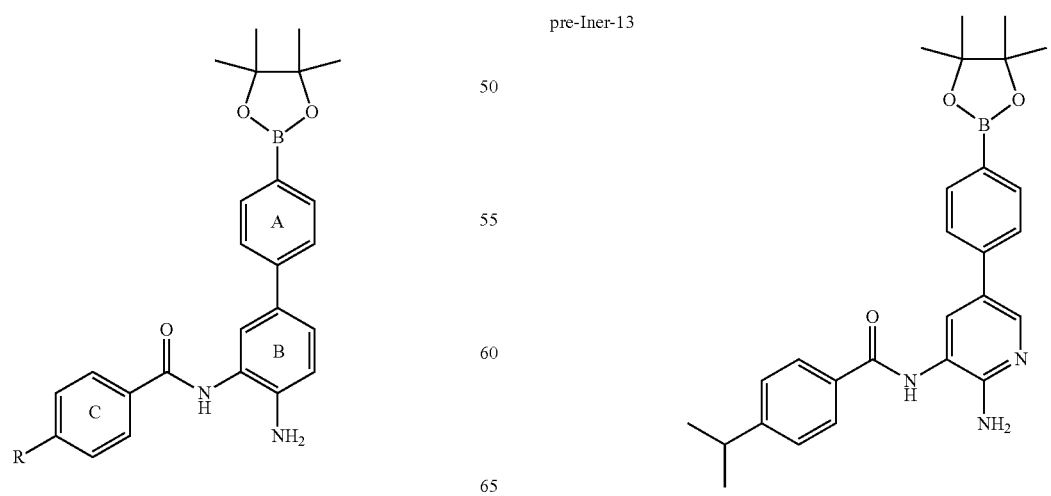
TABLE 2-2
| Code | Structure |
|---|---|
| pre-Iner-11 | 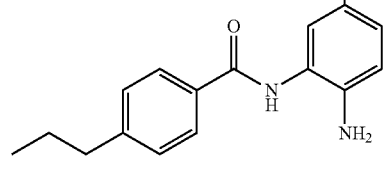 |
| pre-Iner-12 | 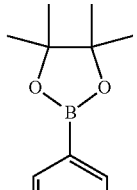 |
| pre-Iner-13 | 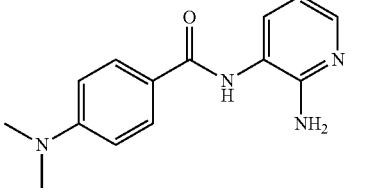 |

TABLE 2-2-continued
| Code | Structure |
|------|-----------|
| pre-Iner-14 | 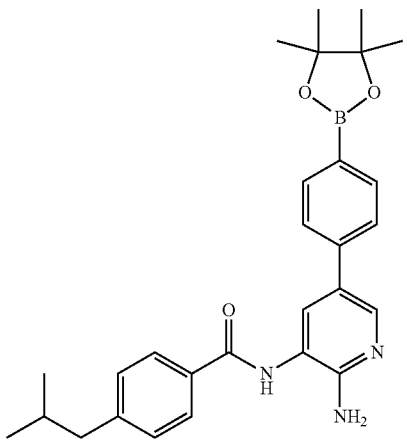 |
| pre-Iner-15 | 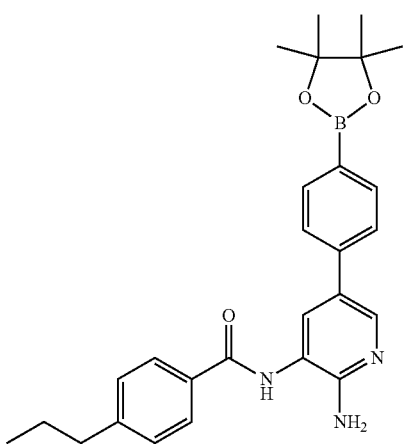 [SMILES: CCCc1ccc(C(=O)Nc2cc(-c3ccc(B4OC(C)(C)C(C)(C)O4)cc3)cnc2N)cc1] |
| pre-Iner-16 | 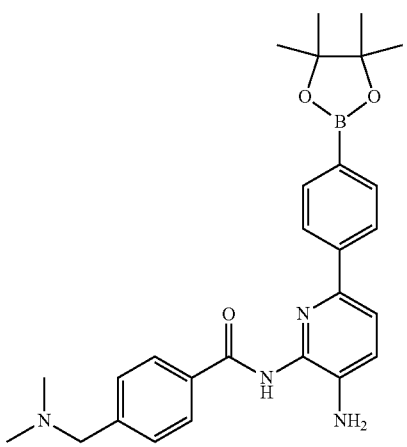 |
TABLE 2-2-continued
| Code | Structure |
|------|-----------|
| pre-Iner-17 | 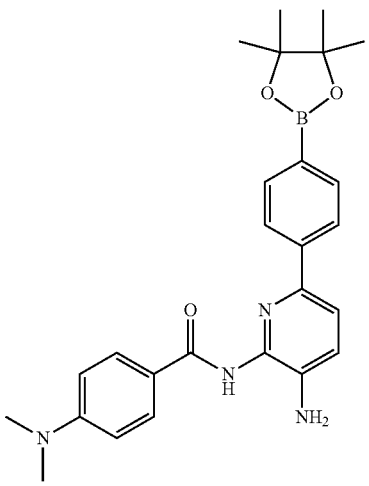 |
| pre-Iner-18 | 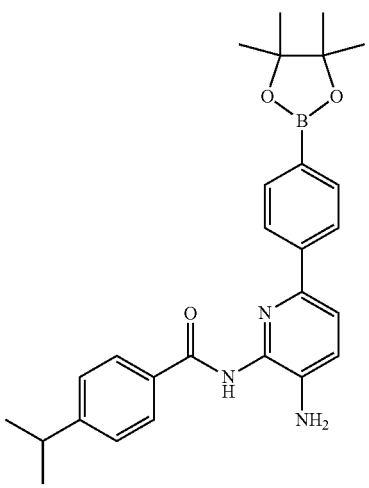 |
| pre-Iner-19 | 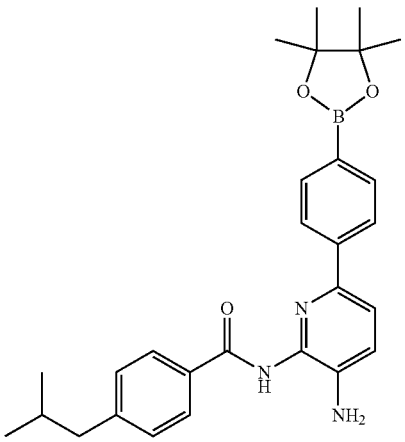 [SMILES: CC(C)Cc1ccc(C(=O)Nc2nc(-c3ccc(B4OC(C)(C)C(C)(C)O4)cc3)ccc2N)cc1] |

TABLE 2-2-continued
| Code | Structure |
|---|---|
| pre-Iner-20 | 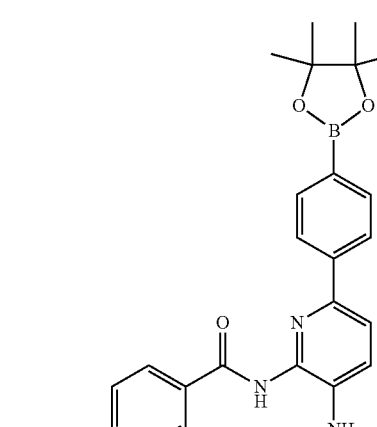 |
3. Replacing C ring of Benzene with Pyridine, as follows:
TABLE 2-3
| Code | Structure |
|---|---|
| Iner-21 | |
| Iner-22 | 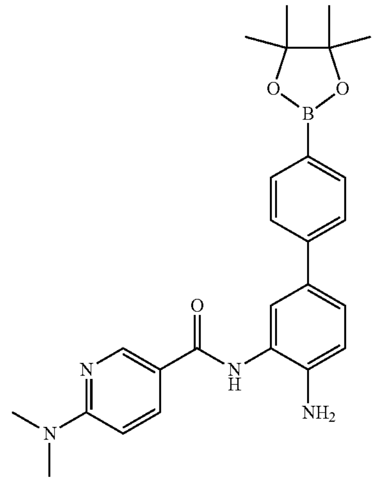 |
| Iner-23 | 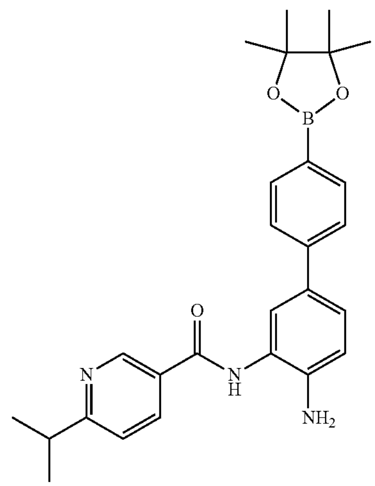 [SMILES: CC(C)c1ccc(C(=O)Nc2cc(-c3ccc(B4OC(C)(C)C(C)(C)O4)cc3)ccc2N)cn1] |
| Iner-24 | 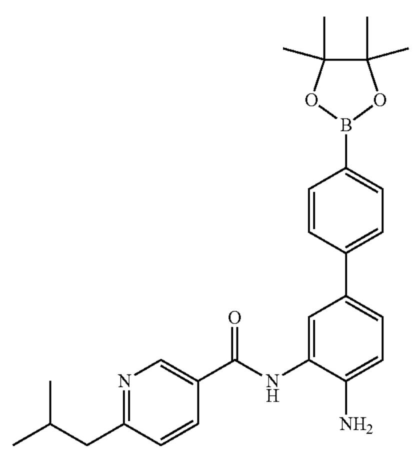 [SMILES: CC(C)Cc1ccc(C(=O)Nc2cc(-c3ccc(B4OC(C)(C)C(C)(C)O4)cc3)ccc2N)cn1] |

TABLE 2-3-continued

| Code | Structure |
|---|---|
| Iner-25 | (structure) |
| Iner-26 | (structure) |
| Iner-27 | (structure) |
| Iner-28 | (structure) |
| Iner-29 | (structure) |
| Iner-30 | (structure) |

The group 3 of the precursors having HDAC inhibitor BNL-26 and the indole/indoline derivatives, as shown in the following Table 3: (* indicates the bonding position)

TABLE 3

| Code | A | R1 | R2 | R3 |
|---|---|---|---|---|
| preindo-1 | 2,5-disubstituted aniline (R1 top, R2 bottom, HN-) | 4-(pinacolboronate)phenyl | *NH2 | indolin-1-yl |
| preindo-2 | 2,3-disubstituted 6-aminopyridine | 4-(pinacolboronate)phenyl | *NH2 | indolin-1-yl |
| preindo-3 | 2,5-disubstituted aniline | 5-(pinacolboronate)pyridin-2-yl | *NH2 | indolin-1-yl |
| preindo-4 | 2,5-disubstituted aniline | phenyl | *HN-CH2CH2-OsT | indolin-1-yl |

TABLE 3-continued

| Code | A | R1 | R2 | R3 |
|---|---|---|---|---|
| preindo-5 | R₁, R₂ substituted phenyl with HN | phenyl | HN-CH₂-C≡C-OsT | indoline |
| preindo-6 | R₁, R₂ substituted 2-aminopyridine | phenyl | HN-CH₂CH₂-OsT | indoline |
| preindo-7 | R₁, R₂ substituted phenyl with HN | phenyl-Bpin | *NH₂ | indole |
| preindo-8 | R₁, R₂ substituted 2-aminopyridine | phenyl-Bpin | *NH₂ | indole |

TABLE 3-continued

| Code | A | R1 | R2 | R3 |
|---|---|---|---|---|
| preindo-9 | 2,5-disubstituted aniline (R1, R2) | 5-(4,4,5,5-tetramethyl-1,3,2-dioxaborolan-2-yl)pyridin-2-yl | *NH2 | indol-1-yl |
| preindo-10 | 2,5-disubstituted aniline (R1, R2) | phenyl | *HN-CH2CH2-OsT | indol-1-yl |
| preindo-11 | 2,5-disubstituted aniline (R1, R2) | phenyl | *HN-CH2-C≡C-OsT | indol-1-yl |
| preindo-12 | 2,3,6-trisubstituted pyridin-2-amine (R1, R2) | phenyl | *HN-CH2CH2-OsT | indol-1-yl |

The precursors shown above are synthesized with steps listed in the Table 4 below.
TABLE 4
| R | Group | Scheme |
|---|---|---|
| R1 | 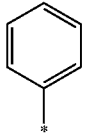 | 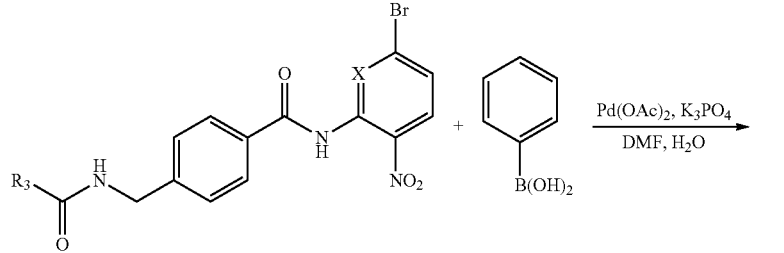 |
| | 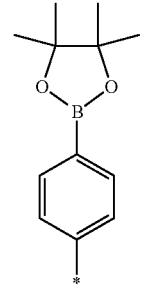 | 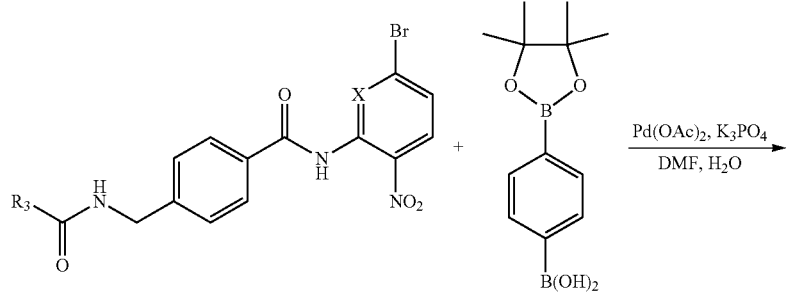 |

TABLE 4-continued
| R | Group | Scheme |
|---|---|---|
| | | 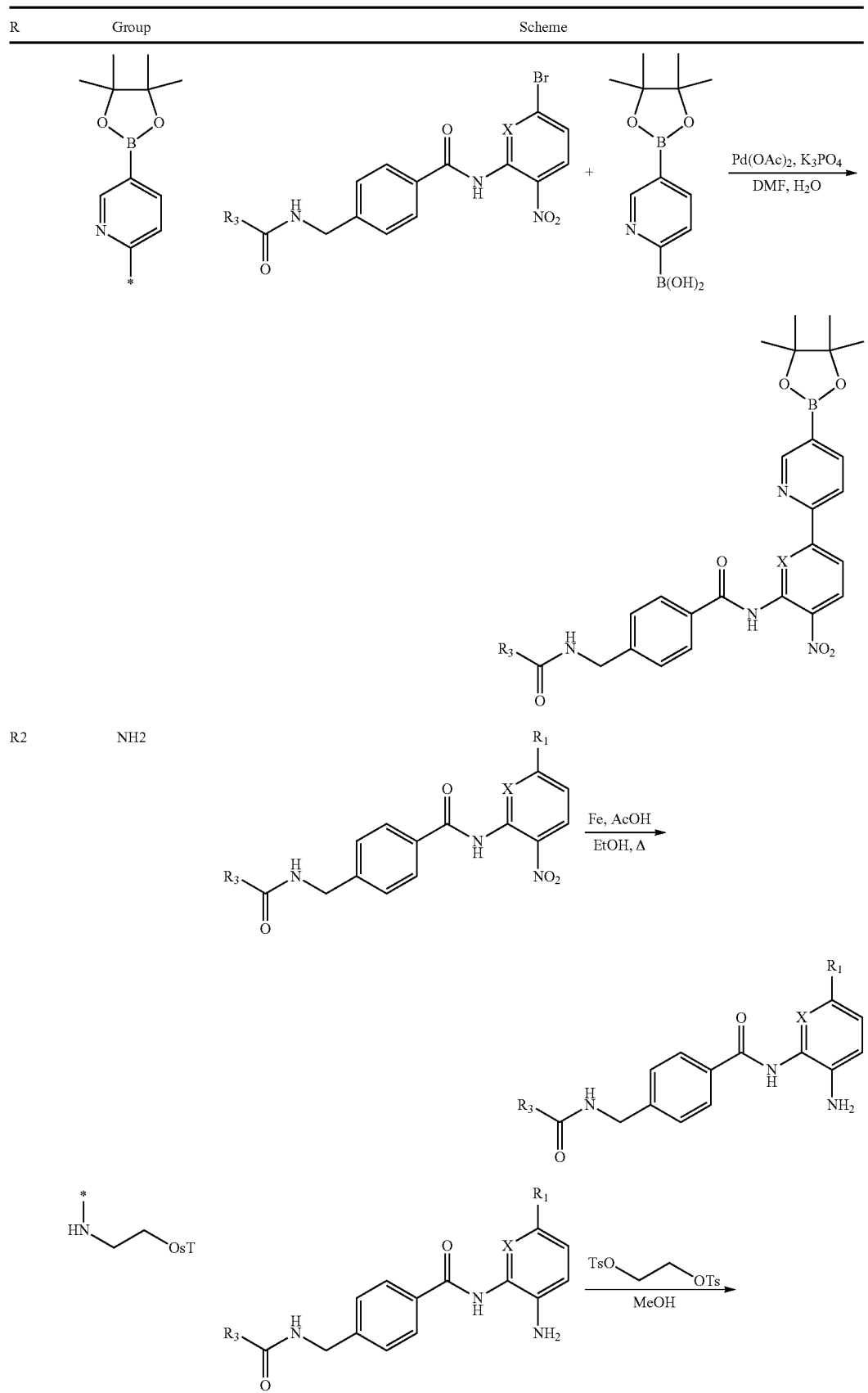 |
| R2 | NH2 | |

TABLE 4-continued

| R | Group | Scheme |
|---|---|---|
| | | |
| R3 | Indole | |
| | Indoline | |

Whether the tumor and brain degenerative disease can be detected, diagnosed and treated in a timely manner depends on the diagnostic method used. The latest advances in molecular biology have started up several new ways for the detection, diagnosis and treatment of malignant tumors. Although these new ways are still in the process of research, but the prospects are very promising. Using these new detection methods, it can be found in the subtle changes in cells and can be found earlier for malignant tumors. Such new technologies also contribute to the development of treatment regimens, which are based on individual differences in patients and towards the scientific goal of individualized treatment.

What is claimed is:

1. A compound selected from group 1 or group 2, wherein group 1 is selected from the group consisting of:

| Code | IUPAC | Structure |
|---|---|---|
| pre-BNL-26 | N-(4-amino-4'-(4,4,5,5-tetramethyl-1,3,2-dioxaborolan-2-yl)-[1,1'-biphenyl]-3-yl)-4-((dimethylamino)methyl)benzamide | 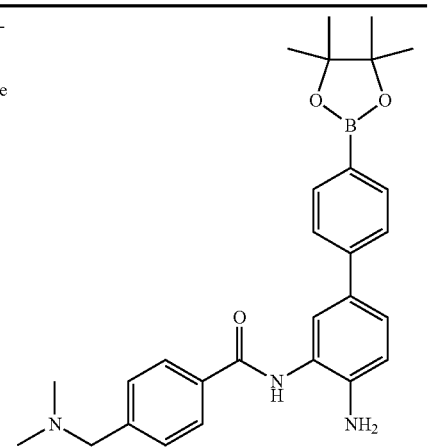 |
| pre-BNL-26a | N-(4-amino-4'-(4,4,5,5-tetramethyl-1,3,2-dioxaborolan-2-yl)-[1,1'-biphenyl]-3-yl)-4-(dimethylamino)benzamide | 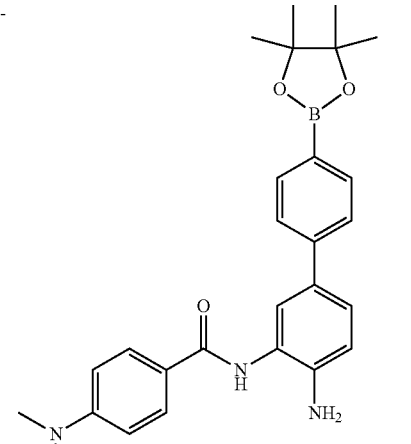 |
| pre-BNL-26b | N-(4-amino-4'-(4,4,5,5-tetramethyl-1,3,2-dioxaborolan-2-yl)-[1,1'-biphenyl]-3-yl)-4-isopropylbenzamide | 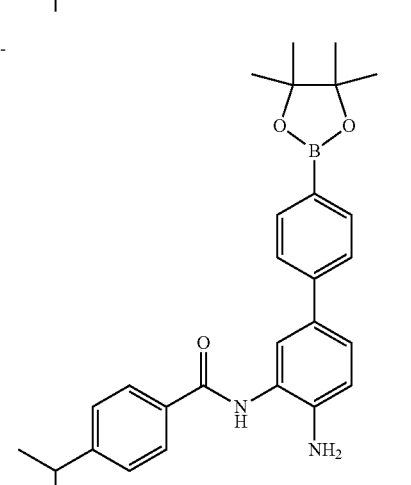 |

| Code | IUPAC | Structure |
|---|---|---|
| pre-BNL-26c | N-(4-amino-4'-(4,4,5,5-tetramethyl-1,3,2-dioxaborolan-2-yl)-[1,1'-biphenyl]-3-yl)-4-isobutylbenzamide | 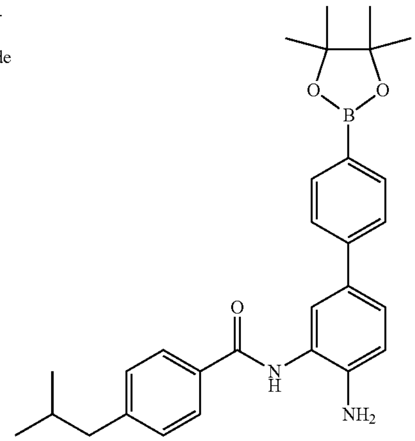 |
| pre-BNL-26d | N-(4-amino-4'-(4,4,5,5-tetramethyl-1,3,2-dioxaborolan-2-yl)-[1,1'-biphenyl]-3-yl)-4-propylbenzamide | | wherein group 2 is selected from the group consisting of:

| Code | IUPAC | Structure |
|---|---|---|
| preindo-1 | N-(4-((4-amino-4'-(4,4,5,5-tetramethyl-1,3,2-dioxaborolan-2-yl)-[1,1'-biphenyl]-3-yl)carbamoyl)benzyl)indoline-1-carboxamide | 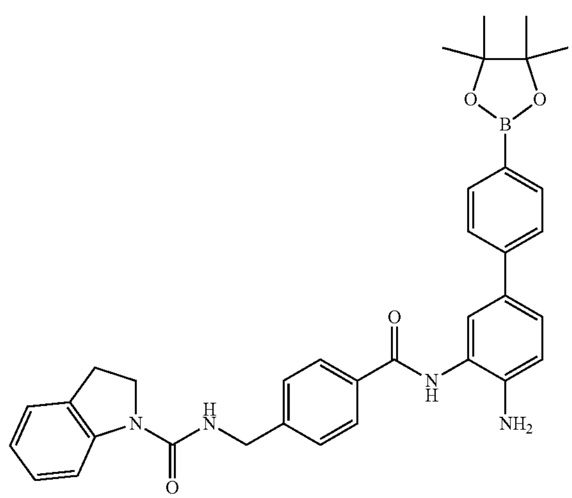 [SMILES: CC1(C)OB(c2ccc(-c3ccc(N)c(NC(=O)c4ccc(CNC(=O)N5CCc6ccccc65)cc4)c3)cc2)OC1(C)C] |

| Code | IUPAC | Structure |
|---|---|---|
| preindo-2 | N-(4-((3-amino-6-(4-(4,4,5,5-tetramethyl-1,3,2-dioxaborolan-2-yl)phenyl)pyridin-2-yl)carbamoyl)benzyl)indoline-1-carboxamide | 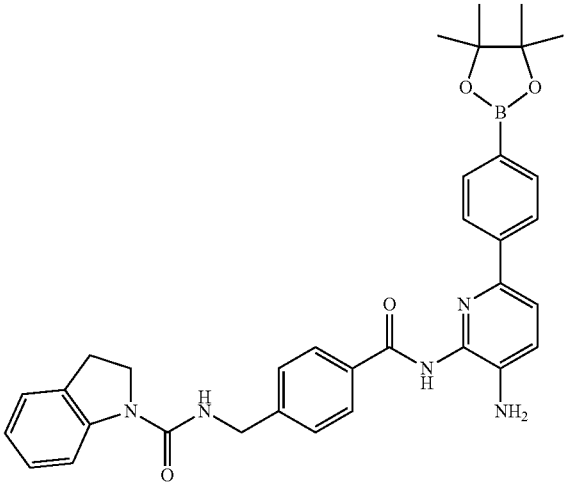 [SMILES: CC1(C)OB(c2ccc(-c3ccc(N)c(NC(=O)c4ccc(CNC(=O)N5CCc6ccccc65)cc4)n3)cc2)OC1(C)C] |
| preindo-3 | N-(4-((2-amino-5-(5-(4,4,5,5-tetramethyl-1,3,2-dioxaborolan-2-yl)pyridin-2-yl)phenyl)carbamoyl)benzyl)indoline-1-carboxamide | 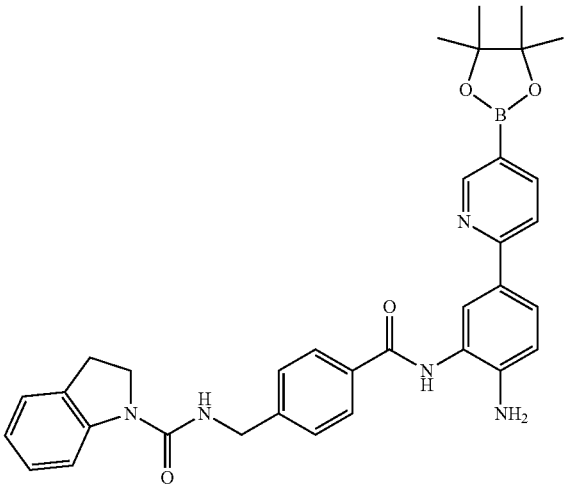 [SMILES: CC1(C)OB(c2ccc(-c3ccc(N)c(NC(=O)c4ccc(CNC(=O)N5CCc6ccccc65)cc4)c3)nc2)OC1(C)C] |
| preindo-4 | 2-((3-(4-((indoline-1-carboxamido)methyl)benzamido)-[1,1'-biphenyl]-4-yl)amino)ethyl 4-methylbenzenesulfonate | 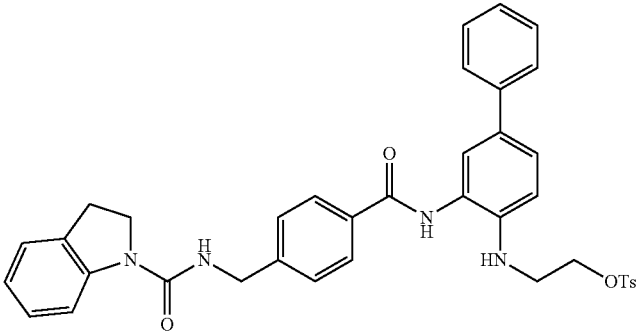 |

| Code | IUPAC | Structure |
|---|---|---|
| preindo-5 | 3-((3-(4-((indoline-1-carboxamido)methyl)benzamido)-[1,1'-biphenyl]-4-yl)amino)prop-1-yn-1-yl 4-methylbenzenesulfonate | 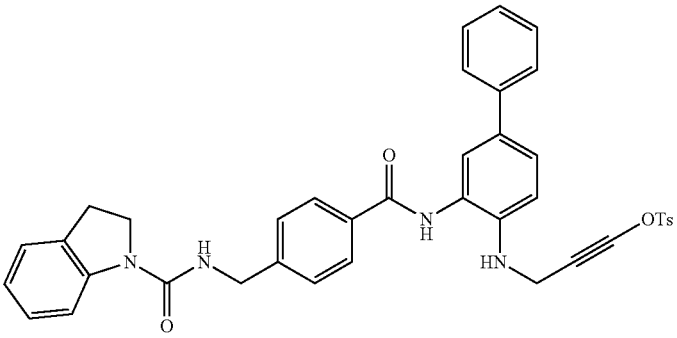 [SMILES: Cc1ccc(S(=O)(=O)OC#CCNc2ccc(-c3ccccc3)cc2NC(=O)c2ccc(CNC(=O)N3CCc4ccccc43)cc2)cc1] |
| preindo-6 | 2-((2-(4-((indoline-1-carboxamido)methyl)benzamido)-6-phenylpyridin-3-yl)amino)ethyl 4-methylbenzenesulfonate | 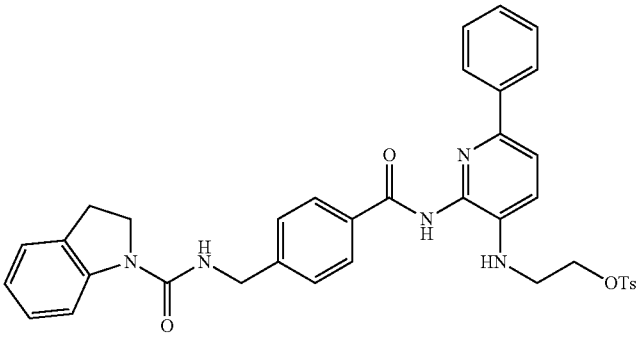 [SMILES: Cc1ccc(S(=O)(=O)OCCNc2ccc(-c3ccccc3)nc2NC(=O)c2ccc(CNC(=O)N3CCc4ccccc43)cc2)cc1] |
| preindo-7 | N-(4-((4-amino-4'-(4,4,5,5-tetramethyl-1,3,2-dioxaborolan-2-yl)-[1,1'-biphenyl]-3-yl)carbamoyl)benzyl)-1H-indole-1-carboxamide | 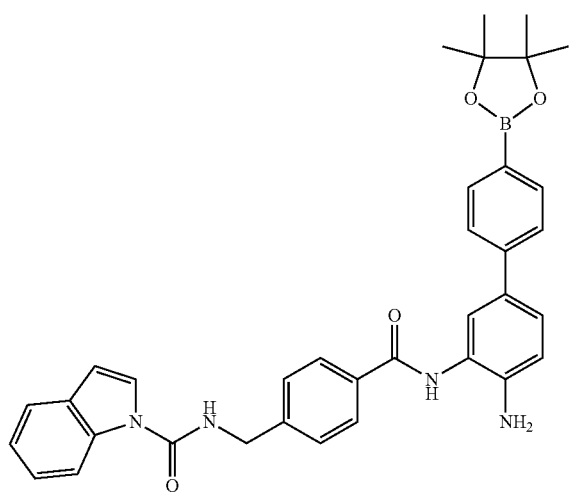 [SMILES: CC1(C)OB(c2ccc(-c3ccc(N)c(NC(=O)c4ccc(CNC(=O)n5ccc6ccccc65)cc4)c3)cc2)OC1(C)C] |

-continued
| Code | IUPAC | Structure |
|------|-------|-----------|
| preindo-8 | N-(4-((3-amino-6-(4-(4,4,5,5-tetramethyl-1,3,2-dioxaborolan-2-yl)phenyl)pyridin-2-yl)carbamoyl)benzyl)-1H-indole-1-carboxamide | 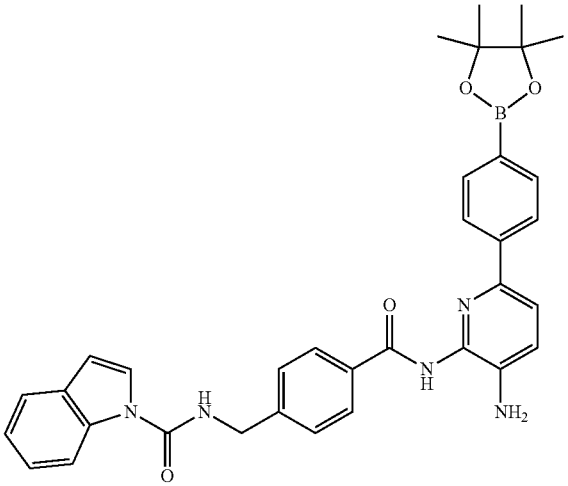 [SMILES: CC1(C)OB(c2ccc(-c3ccc(N)c(NC(=O)c4ccc(CNC(=O)n5ccc6ccccc65)cc4)n3)cc2)OC1(C)C] |
| preindo-9 | N-(4-((2-amino-5-(5-(4,4,5,5-tetramethyl-1,3,2-dioxaborolan-2-yl)pyridin-2-yl)phenyl)carbamoyl)benzyl)-1H-indole-1-carboxamide | 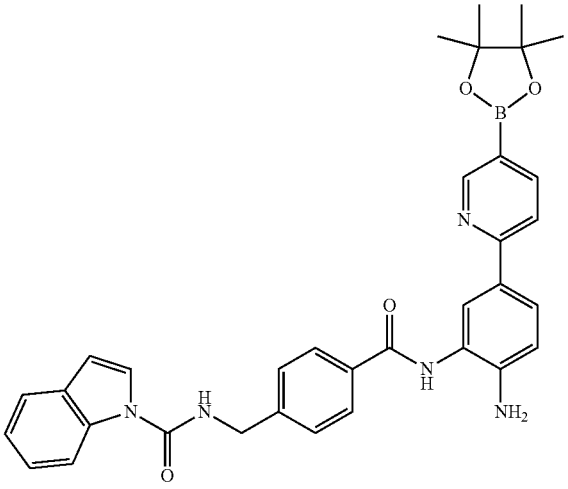 [SMILES: CC1(C)OB(c2ccc(-c3ccc(N)c(NC(=O)c4ccc(CNC(=O)n5ccc6ccccc65)cc4)c3)nc2)OC1(C)C] |
| preindo-10 | 2-((3-(4-((1H-indole-1-carboxamido)methyl)benzamido)-[1,1'-biphenyl]-4-yl)amino)ethyl 4-methylbenzenesulfonate | 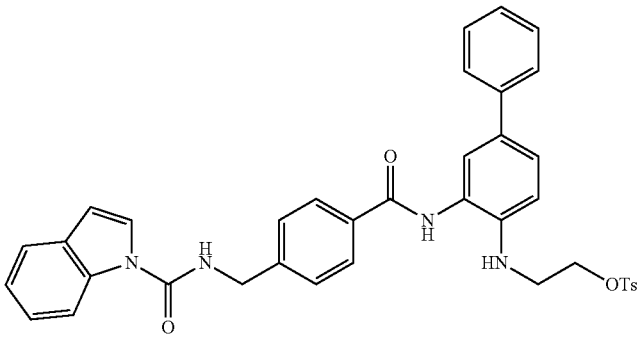 |

-continued
| Code | IUPAC | Structure |
|---|---|---|
| preindo-11 | 3-((3-(4-((1H-indole-1-carboxamido)methyl)benzamido)-[1,1'-biphenyl]-4-yl)amino)prop-1-yn-1-yl 4-methylbenzenesulfonate | 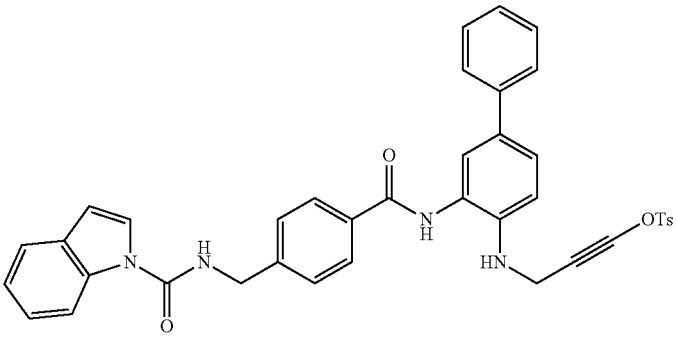 |
| preindo-12 | 2-((2-(4-((1H-indole-1-carboxamido)methyl)benzamido)-6-phenylpyridin-3-yl)amino)ethyl 4-methylbenzenesulfonate | 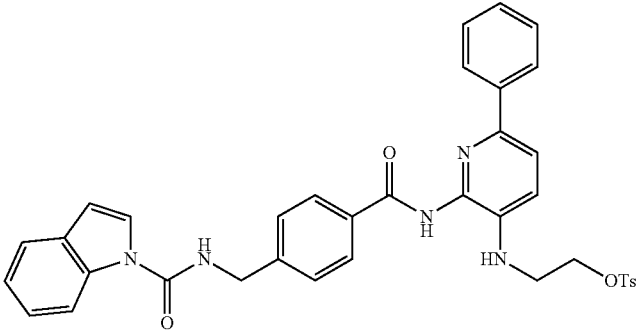 [SMILES: Cc1ccc(S(=O)(=O)OCCNc2ccc(-c3ccccc3)cc2NC(=O)c2ccc(CNC(=O)n3ccc4ccccc43)cc2)cc1] |
\* \* \* \* \*